United States Patent
Hughes

(10) Patent No.: US 6,663,547 B1
(45) Date of Patent: Dec. 16, 2003

(54) CONFIGURABLE PUSH-UP DEVICE

(76) Inventor: John P. Hughes, 12814 Wrexham Rd., Herndon, VA (US) 20171-2401

( * ) Notice: Subject to any disclaimer, the term of this patent is extended or adjusted under 35 U.S.C. 154(b) by 0 days.

(21) Appl. No.: 10/208,037

(22) Filed: Jul. 31, 2002

(51) Int. Cl.⁷ .......................... A63B 26/00; A63B 71/00
(52) U.S. Cl. ...................... 482/141; 482/62; 482/148
(58) Field of Search ................................ 482/141, 148, 482/62, 140, 907, 908, 14–23, 67, 63, 121–130

(56) References Cited

U.S. PATENT DOCUMENTS

| | | | | |
|---|---|---|---|---|
| 4,323,234 A | * | 4/1982 | Glaese ......................... | 272/93 |
| 4,923,194 A | * | 5/1990 | Montgomery ................ | 272/93 |
| 5,690,597 A | * | 11/1997 | Enfaradi ...................... | 482/126 |
| 5,913,756 A | * | 6/1999 | Glaser ......................... | 482/128 |

* cited by examiner

*Primary Examiner*—Nicholas D. Lucchesi
*Assistant Examiner*—L Amerson
(74) *Attorney, Agent, or Firm*—Roberts, Mlotkowski & Hobbes; Charles Lobsenz

(57) ABSTRACT

The present invention comprises a novel push-up device which is configurable by user body characteristics and by predetermined conditions for range of motion so as to guide an exerciser to perform a push-up which meets such predetermined range of motion and exercise form criteria. Through the use of the device of the present invention, exercisers are able to perform push-ups that meet predetermined range of motion criteria regardless of their body characteristics and receive feedback based upon whether the exercise was properly performed or not.

15 Claims, 4 Drawing Sheets

CONFIGURABLE PUSH-UP DEVICE

BACKGROUND

1. Field of the Invention

The present invention relates generally to exercise devices and more particularly to a device for performing push-ups according to standardized requirements.

2. Background of the Invention

It is well known that exercise is an important aspect of maintaining a healthy body and confronting the effects of aging. Many educators and physical fitness professionals believe that a life-long commitment to physical fitness is best promoted by encouraging participation at an early age. One manifestation of this belief is the presence of physical education programs in the vast majority of schools within the United States and elsewhere.

In response to a concern that American children scored lower than their European counterparts on a battery of physical fitness tests, the President's Council on Youth Fitness was founded on Jul. 16, 1956 to encourage American children to lead healthy, active and physically fit lives. The council has evolved over the years and is presently known as the President's Council on Physical Fitness and Sports (PCPFS).

One aspect of the PCPFS's mission is the administration of the "President's Challenge" program. During the 2000–2001 school year, more than 30,000 schools took part in this program and more than 4 million children participated. One program component of the overall President's Challenge program is the "Physical Fitness" component. This program calls for children to participate in a battery of physical fitness tests that include tests such as those known as "Curl-ups", "Shuttle run", "Endurance run", "V-sit Reach", "Pull-ups", "Sit and Reach" and "Right Angle Push-Ups".

Students may elect among alternative exercises in some cases but they must meet the minimum requirements in order to receive an award. Awards vary based upon qualifying standards. For example, in order to receive the "Presidential Physical Fitness Award" boys and girls must score above the 85$^{th}$ percentile on five tests. The "National Physical Fitness Award" is given to those that score above the 50$^{th}$ percentile on these five tests. States and various organizations may also offer other awards based upon specific qualifying criteria. For example, Virginia offers the "Virginia Wellness Award" to students in Virginia schools that meet specified criteria that do not rise to the level of the "Presidential Physical Fitness Award" or the "National Physical Fitness Award".

While the tests are relatively easy to administer to the children, unfortunately, some level of subjectivity exists in connection with the performance of the tests. As a result, children sometimes tend to either intentionally or unintentionally exploit this subjectivity in order to achieve performance levels that they might not be able to obtain if the exercises were down according to proper standards and form. For example, in the case of right angle push-ups, the proper form (and the most difficult way to perform the exercise) occurs when the student's lower arms are at a substantially right angle with their shoulders during the range of motion. The proper exercise motion also requires students to start by lying face down on a mat or on the floor in push-up position with hands under shoulders, fingers straight, and legs straight, parallel, and slightly apart, and with the toes supporting the feet. The student should then straighten his or her arms while keeping his or her back and knees straight, and then the student should lower the body until there is a 90-degree angle at the elbows, with the upper arms parallel to the floor. The student should go down at least until there is a 90 degree bend at the elbows and then back up.

Various ways of doing the exercise such that they deviate from proper form can make the exercise both easier to do and less effective as an indicator of upper body strength. For example, students may seek to count as a full push up, a motion that is significantly less than the desirable range of motion described above. Alternatively, students may perform the complete range of motion but only with one side of their body (i.e. only one shoulder goes down to the required bottom of motion rather, than both).

In addition to the above described physical fitness testing that occurs in schools in connection with the Presidential Physical Fitness program and otherwise, various other contexts call for physical fitness testing and in particular physical fitness testing wherein subjective exercises can be more easily controlled to ensure that exercises are being performed according to a defined form and procedure. For example, military training situations such as boot camp and ongoing physical training exercises and evaluation call for at least some level of objective measurement and evaluation.

SUMMARY OF THE INVENTION

It is therefore a primary object of the present invention to provide a device which allows a user or an observer to engage in, or observe, respectively, a controlled motion push-up exercise meeting specific range of motion criteria.

It is another object of the present invention to provide a portable and user-friendly device which provides direct feedback on range of motion during a push-up exercise.

It is yet another object of the present invention to provide a push-up device which provides feedback to an exerciser with respect to push-ups meeting the specific range of motion criteria.

It is a still further object of the present invention to provide a device which is easily customizable for use by exercisers with a variety of body configurations including different arm sizes, different shoulder widths and different heights.

It is a further object of the present invention to provide a device that guides an exerciser toward a push-up range of motion through which the exerciser can gain maximum benefit in terms of exercise results.

These and other objects of the present invention are obtained through the use of a push-up device which is configurable by user body characteristics and by predetermined conditions for range of motion so as to guide an exerciser to perform a push-up which meets such predetermined range of motion and exercise form criteria. Through the use of the device of the present invention, exercisers are able to perform push-ups that meet predetermined range of motion criteria regardless of their body characteristics and receive feedback based upon whether the exercise was properly performed or not.

According to a preferred embodiment of the invention, the push-up exercise device described herein consists of three primary components. The first component of the push-up exercise device of the present invention is a push-up Guide Box. The Guide Box is placed on the floor or on a mat and the exerciser performs push-ups above two guide legs extending from the Guide Box component of the device. The Guide Box also preferably contains an audible feedback means such as a bell which rings when a push-up with the correct range of motion is performed. A buzzer or other sound making device may also be used as may a digital counter which registers the number of push-ups. A second component of the device comprises an arm length/shoulder width sizing unit (Sizing Unit). The Sizing Unit is employed to configure the Guide Box according to specific user body characteristics so that the proper range of motion for the push-up exercise is obtained. The final component of the push-up exercise device is a set of Arm Length Extenders which are selected based upon measurements obtained from the Sizing Unit for a particular individual's body characteristics. Based upon measurements obtained from t Sizing Unit, a pair of Arm Length Extenders are selected and placed in the appropriate location in the Guide Box Legs in preparation for the push-up exercise.

As will be described in greater detail below, the device comprising the present invention offers a number of advantages and may be employed in a variety of contexts. For example, the device may be configured so that those performing push-ups using the device of the present invention are necessarily meeting the required format and range of motion required to obtain awards such as the President's Challenge Physical Fitness award. Alternatively, the device may be employed in applications where it is necessary or desirable to ensure that those doing push-ups are using a form and range of motion that meets pre-defined standards such as in connection with physical fitness evaluations conducted in the military context. The device of the present invention further provides the ability to guide exercisers toward push-ups that are the most beneficial in terms of training results regardless of whether testing or evaluation is being performed or not.

These and other advantages and features of the present invention are described herein with specificity so as to make the present invention understandable to one of ordinary skill in the art.

DETAILED DESCRIPTION OF THE INVENTION

Figure 1:
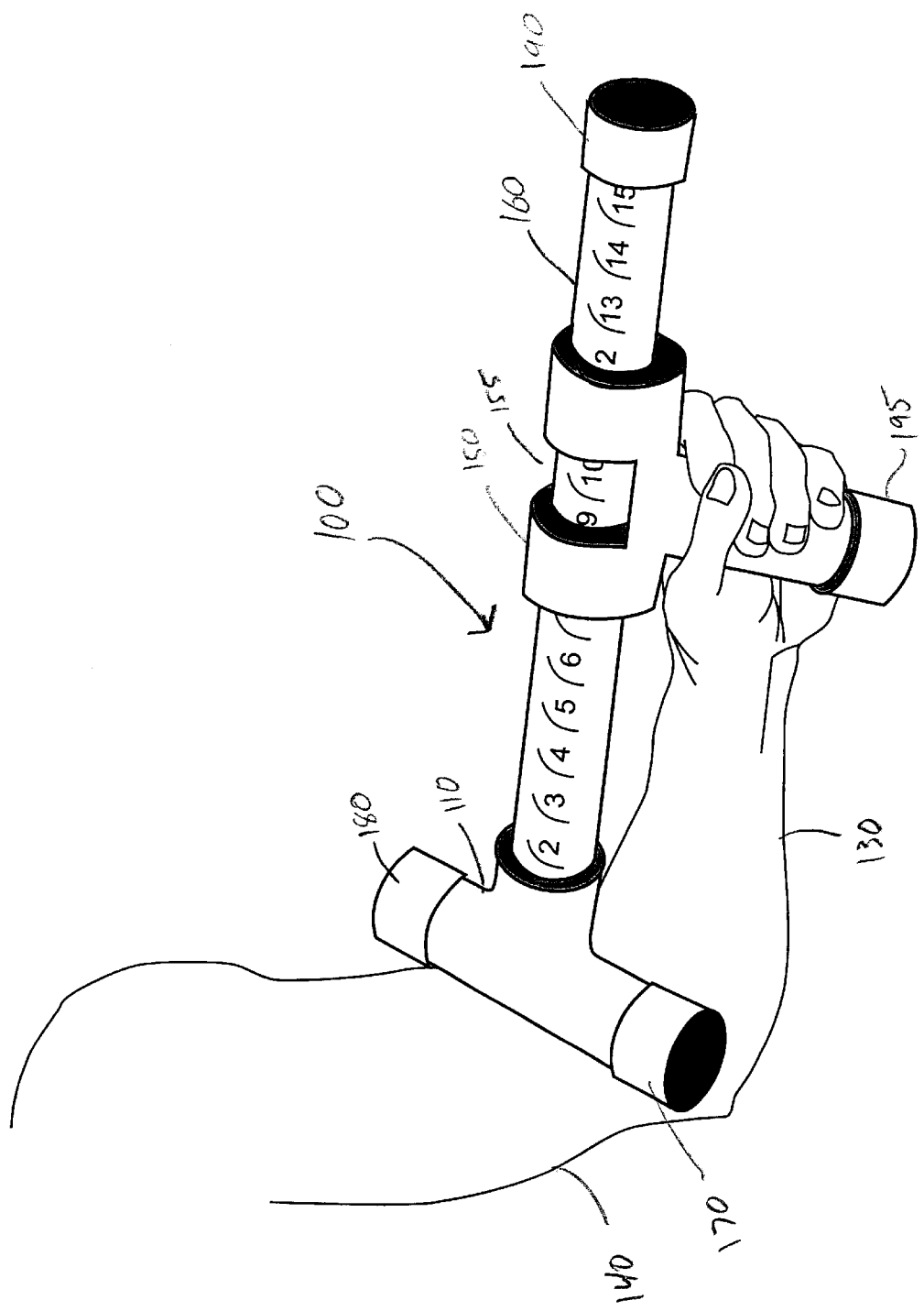
FIG. 1 is an illustration showing the Sizing Unit component of the present invention as may be used by an exerciser to measure lower arm length.

The present invention is now described generally to provide the reader with an overview of the device and its use according to the preferred embodiments. Following the general description, a detailed discussion of each of the components, their use and the way they work together is provided.

In general terms, the components of the present invention work together to provide a user with a framework in which he or she can perform a controlled motion push-up. Each of the three primary components of the present invent plays a role in providing this framework and allowing the user to configure the device so as to guide him or her to the push-up range of motion that is desired.

In order to so configure the push-up device of the present invention, the person who will perform the push-up or an assistant (e.g. a physical education teacher, drill sergeant, etc.) runs through the sizing process as now generally described. First, the person who will perform the push-up (referred to herein as the "user") positions the Sizing Unit such that one end rests in the crook of the arm where the lower arm and the upper arm meet (more discussion of the proper positioning as related to the body anatomy is provided below) and a "lower arm" measurement is taken. According to a preferred embodiment of the present invention, color-coded ranges may be used such that they key to the arm length extenders next discussed.

One the "lower arm" measurement is taken and a color code has been obtained for the individual user, the user selects a pair of Arm Length Extenders which are color-coded to match the user's lower arm length range measurement. These Arm Length Extenders are then placed within the receiving area of the two guide legs within the Guide Box component such that the height of the guide legs with the Arm Length Extenders off of the ground generally represents the correct position for the lower range of the push-up motion.

Next, the Sizing Unit is used to take an upper body breadth measurement for the particular user. This measurement is used to position the guide legs of the Guide Box at the correct distance from one another to ensure that at the lower range of the push-up motion, the Arm Length Extenders are contacted by the correct portion of the upper body particular at the base of the rotator cuff in both the left and right shoulders.

Once the Guide Box, and particularly the guide legs containing the appropriate Arm Length Extenders, is correctly positioned as described above, the user commences the performance of push-ups starting from the top of the range, lowering the upper body to the bottom of the range, raising back up to the top of the range and then repeating the motion as many times as possible. The user ranges through this motion while positioned laterally above the guide legs of the Guide Box such that at the bottom of the range of the motion, the base of the user's rotator cuffs at each shoulder contact the respective Arm Length Extender. The motion then continues down slightly further against the pressure of a spring to the point where an audible alarm is activated indicating the completion of a successful push-up meeting the pre-defined range of motion criteria. At this point the user returns to the high point of the range of motion and repeats the process.

Now that the overall process and use of the push-up device of the present invention has been described at a high level, a more detailed description of the components and their use is next provided. FIG. 1 is an illustration of the Sizing Unit component 100 of the present invention showing its use in measuring lower arm length. In preparing for a push-up exercise using the push-up device of the present invention, the user first places Sizing Unit 100 in position as is shown in FIG. 1. As can be seen in the Figure, end piece 110 rests in the portion of the arm where the user's lower arm 130 meets the user's upper arm 140. In order to obtain the best measurement, it is preferred that the user's upper arm 140 make a right angle with the user's lower arm 130 during the measurement. The user grasps hand grip 150 in his or her hand while taking the measurement and moves hand grip 150 by sliding hand grip 150 along inner pipe 160 until the user's lower arm 130 is extended and is at a right angle with the user's upper arm 140 or as close thereto as possible.

Figure 2:
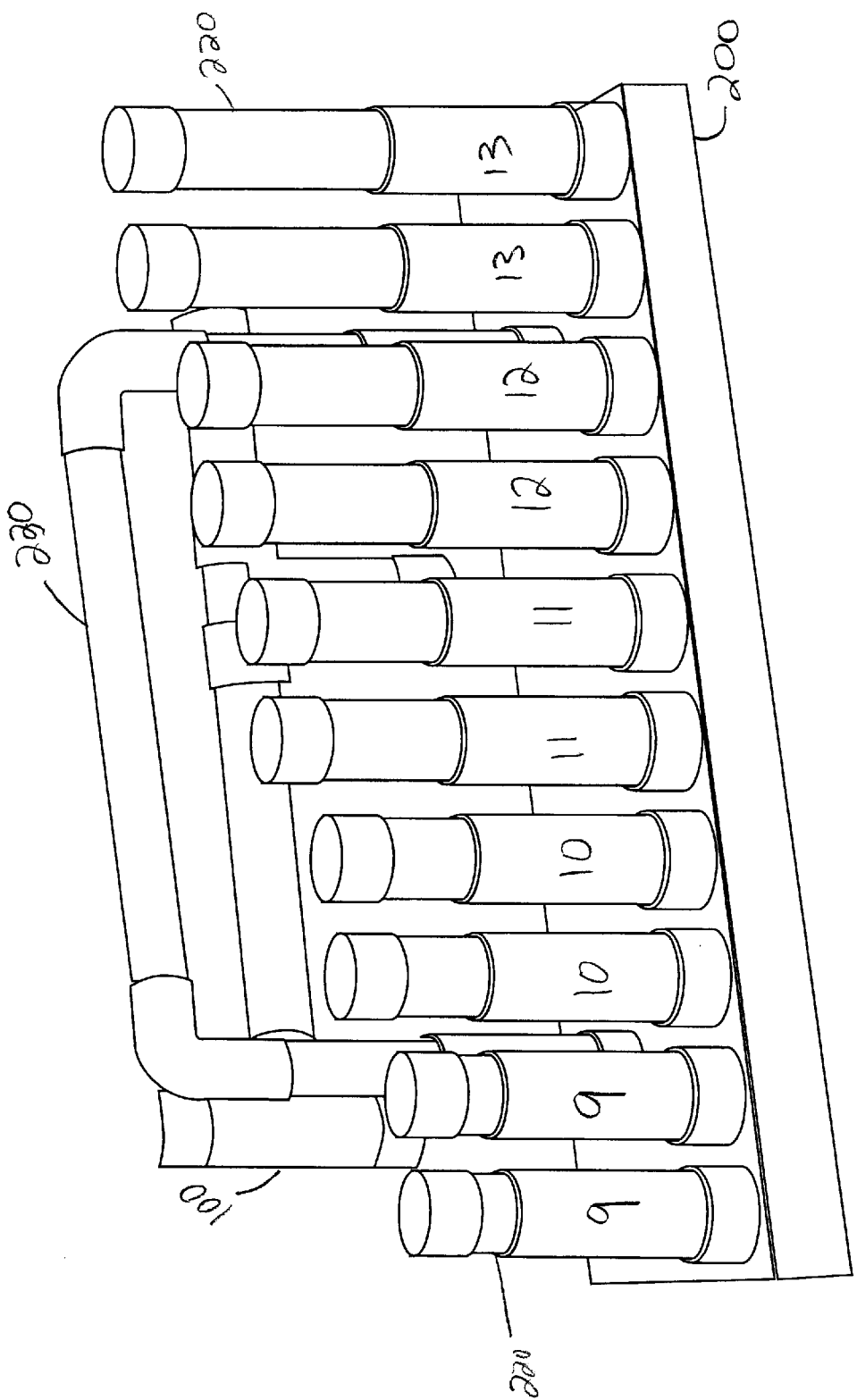
FIG. 2 is an illustration of the Arm Length Extender component of the present invention as housed by a carrying unit.

At this point, a measurement, which is reflective of the length of the user's lower arm 130 generally extending from just below the bicep to the middle of the user's palm, may be taken and read through window 155. Although not shown, hand grip 150 and particularly the ranging window 155 thereof may contain a needle or some other pointing device which points to the measurement scale on inner pipe 160 in order to obtain an accurate reading. The measurement is typically taken in inches but may be taken in any other unit of measure so long as the associated Arm Length Extenders 220 are sized according to the same unit of measure. Arm Length Extenders are shown in FIG. 2. Although only the two outside Arm Length Extenders 220 are labeled as such in FIG. 2, each of the tubes in the Figure are Arm Length Extenders 220 of varying lengths and are present in pairs on the carrying unit 200 shown in FIG. 2. In a preferred embodiment of the present invention, lower arm length ranges are used with each arm length range corresponding to a specific Arm Length Extender 220. Thus, for example, a push-up device according to the present teachings may include five arm length ranges comprising extenders of 9, 10, 11, 12 and 13 inches. For each arm length covered, a pair of Arm Length Extenders 220 are present on carrying unit 200.

In one embodiment of the present invention, Arm Length Extenders 220 may be color coded to various ranges on the measurement scale located on inner pipe 160 of Sizing Unit 100. Thus, for example, the range from 8½ inches to 9½ inches may be color coded black and correspond to the 9" Arm Length Extender pair 220 while the range from 9½ inches to 10½ inches may be color coded red and correspond to the 10" Arm Length Extender pair 220 and so on. Of course other ranges are possible with finer or broader increments depending upon the number of pairs of Arm Length Extenders 220 which are made available.

Sizing Unit 100, may in one embodiment, be constructed from PVC piping which is readily available in home improvement, plumbing stores as well as many other sources. In a preferred embodiment, hand grip 150 is freely slidable over the majority of the length of inner pipe 160. This is accomplished by selecting apertures in hand grip 150 which are just slightly larger in diameter than the diameter of inner pipe 160. Further, plastic end cap 190 ensures that hand grip 150 remains on inner pipe 160. Plastic caps 170, 180 and 195 may also be used in constructing Sizing Unit 100 in order to avoid the appearance of open piping on either end piece 110 or hand grip 150.

As will be readily apparent to one of skill in the art, Sizing Unit 100 may be constructed from many different materials in addition to PVC piping. For example, various metals such as aluminum, may be used. Further, alternate arrangements and configurations for Sizing Unit 100 may also be employed in determining the user's lower arm length without departing from the scope or spirit of the present invention so long as the component employed is able to obtain a reasonably accurate measurement.

Based upon the measurement obtained for lower arm length through the use of Sizing Unit 100, a pair of Arm Length Extenders 220 are selected from the carrying unit 200 and are placed in the guide box leg receptacles in order to reflect the proper height off the floor for the bottom end of the user's range of motion based upon lower arm length. The carrying unit 200 is shown in FIG. 2. As can be seen, the carrying unit 200 not only serves as place to store a plurality of Arm Length Extender pairs, but it may also serve as a holding place for Sizing Unit 100. It may also contain a handle 230 for carrying the set of Arm Length Extenders 220 and the Sizing Unit 100.

Any amount of Arm Length Extenders 220 may be made available and such selection may include various potential sizes depending upon the expected users. For example, in elementary and junior high school applications, a selection of Arm Length Extenders 220 with relatively smaller sizes may be made available while in military applications, the universe of available Arm Length Extenders 220 may include longer sizes.

In the example shown in FIG. 2, the Arm Length Extender 220 selection includes pairs of Arm Length Extenders 220 sized at 9, 10, 11, 12 and 13 inches. This selection is generally a good choice for elementary or middle school applications based upon known typical arm length sizes for children in that age range.

Figure 3:
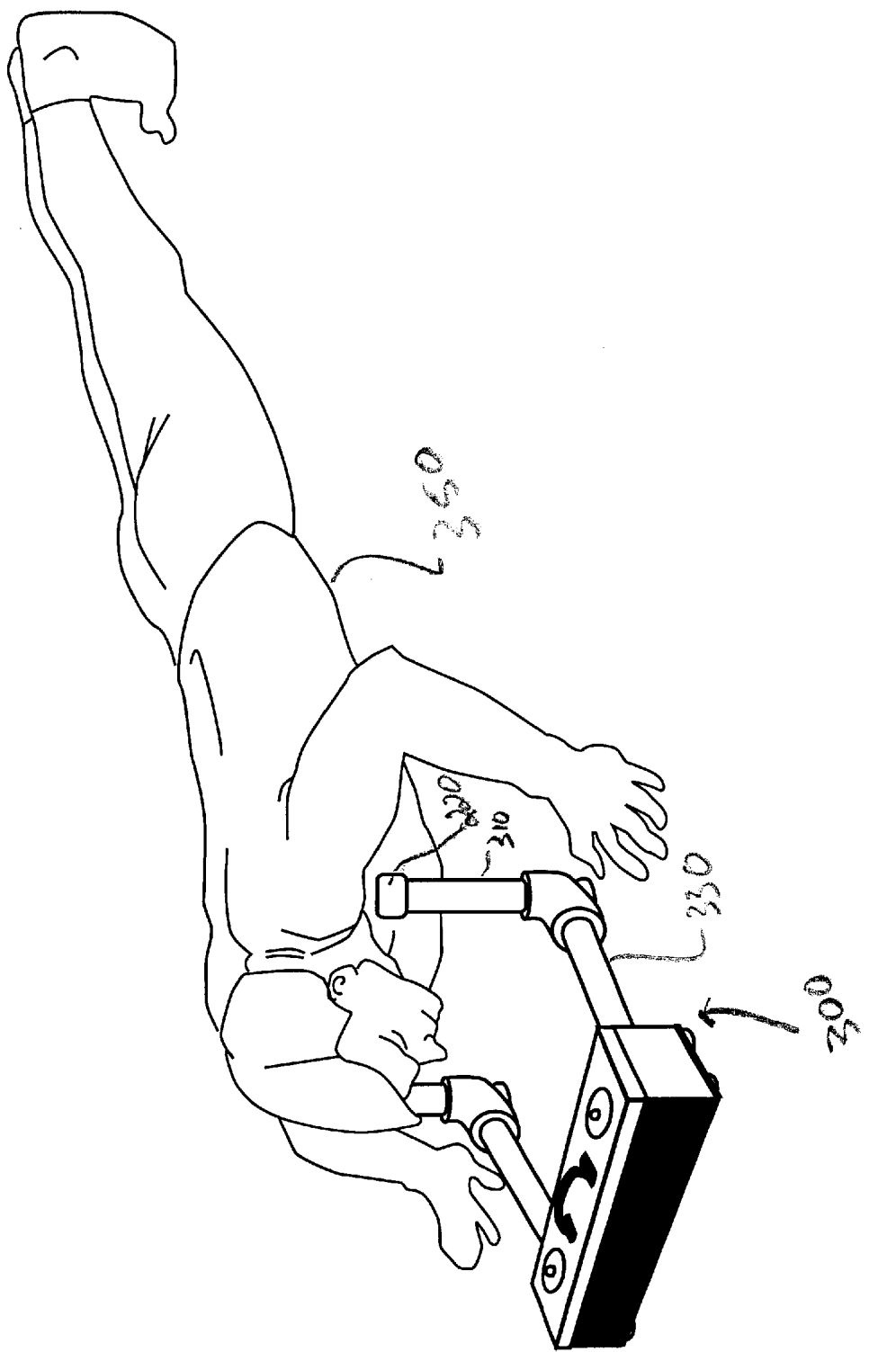
FIG. 3 is an illustration showing an exerciser performing a pushup using the Guide Box component of the device of the present invention.

Turning now to FIG. 3, when a pair of Arm Length Extenders 220 are selected, they are placed in respective hollow tubes 310 comprising the vertical portion of each of a pair of guide legs 330 associated with Guide Box 300. Hollow tubes 310 should be of a sufficient diameter to accept all possible Arm Length Extender pairs 220 that may be used. Guide Box 300 is constructed such that guide legs 330 are movable to adjust the distance between them based upon the upper body breadth measurement taken with Sizing Unit 100. Once the measurement is taken, plastic cap 195 of hand grip 150 is placed on top of one guide leg 330 and either plastic cap 170 or 180 is placed on top of the other guide leg 330 and guide leg distance apart is set such that it matches the upper body breadth measured by Sizing Unit 100.

One the selected Arm Length Extender pair 220 is placed within hollow tubes 310 and the guide legs have been set to the correct distance apart, the exerciser 350 is ready to begin push-up exercises. Exercises are conducted such that exerciser 350 starts at the upper range of motion and then lowers himself or herself down until the upper body region at the base of each respective rotator cuff touches and then slightly pushes down on each of the pair of Arm Length Extenders 220 located within hollow tubes 310.

Figure 4:
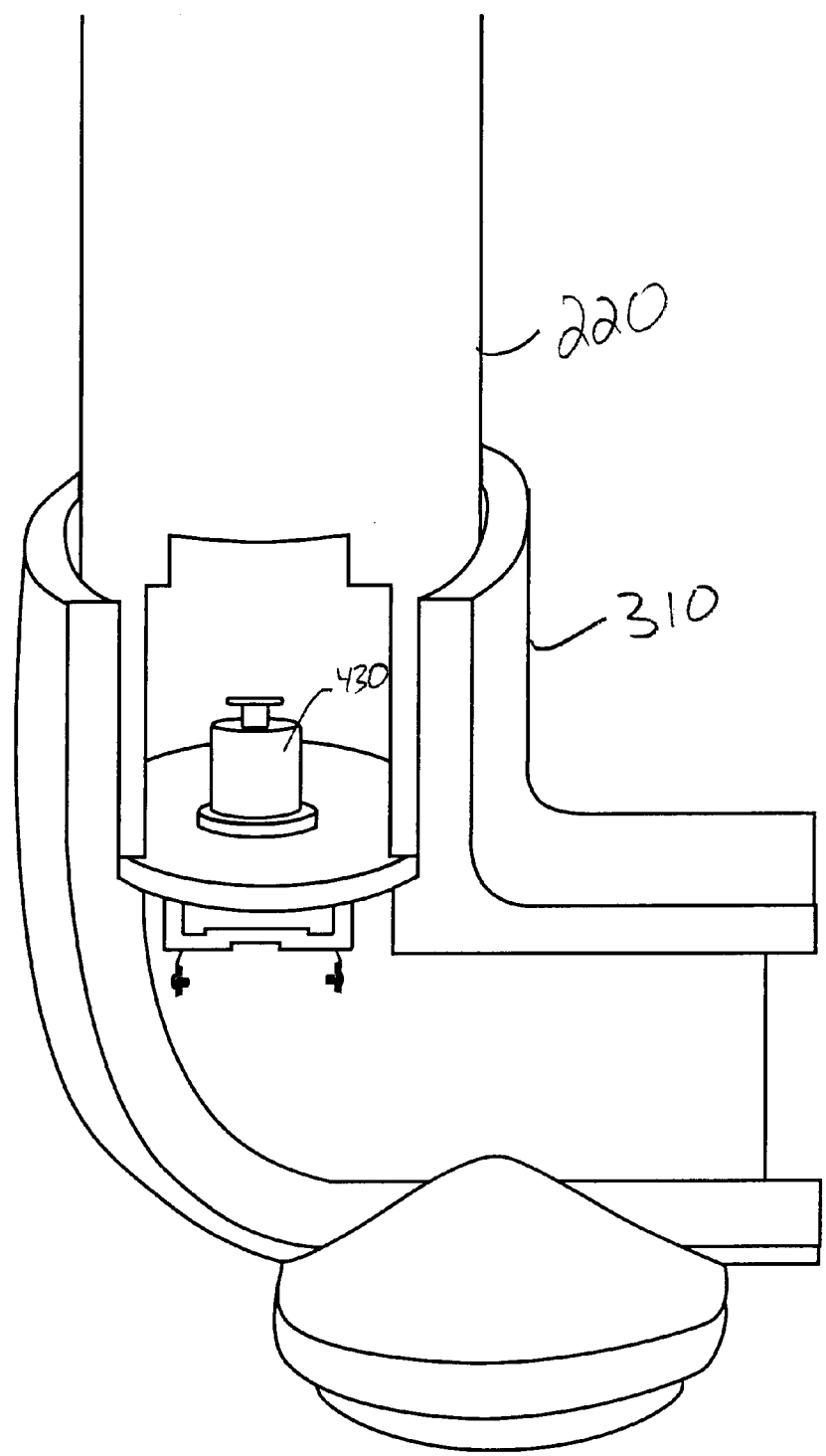
FIG. 4 is an illustration showing a cut-away, close up view of a Guide Box leg particularly in the area containing a switch using in connection with the audible alarm aspect of the present invention.

Arm Length Extenders 220 preferably include a solid base at the bottom which may be constructed from, for example, rubber such as in the case of rubber plug which may be inserted into the bottom of the hollow PVC piping comprising Arm Length Extenders 220. In a preferred embodiment of the invention, push button switch 430 is located at the bottom of hollow tube 310. This is shown in FIG. 4. Push button switch 430 is configured such that when fully depressed, the switch is "on" and a circuit may be completed. Further, in a preferred embodiment, the weight of Arm Length Extender 220 is not sufficient to depress push button switch 430 however, when exerciser 350 performs a push up and contacts and then pushes down Arm Length Extenders 220, push-button switch 430 may be easily and fully depressed. In a preferred embodiment, it is necessary for Arm Length Extender 220 to be pushed down in hollow tube 310 approximately ¼–½ inch in order to fully depress push button switch and close the circuit.

Thus, when exerciser 350 travels in the downward direction and his upper body contacts Arm Length Extenders 220 and then slightly depresses them, a circuit may be completed. In a preferred embodiment, a basic circuit which would be easily understood by one of skill in the art may be constructed such that a bell or some other audible device rings only when both push button switches 430 are depressed simultaneously. This ensures positive feedback only when exerciser 350 fully completes the downward range of motion with respect to both the left and the right sides of the upper body. Other alternatives are also possible such as a circuit in which the audible device only sounds when only one but not both of push button switches 430 are depressed at any moment in time. In this case, an audible alarm would reflect negative feedback that a push-up down motion was completed but only with respect to one side of the upper body.

The audible device (not shown) may comprise a bell which is contained within Guide Box 300. Such a bell and the associated circuit may operate through the use of 9 Volt battery or some other power source which is light weight, easily transportable and offers a reasonable length of time before running out of power.

Additionally, although not shown, the device of the present invention may provide a counter device which counts the number of push-ups performed according to the specified range of motion. Such counters are readily available and substantially the same circuit used for tripping the bell when a push-up is done can also be used for the counter. It is also possible to include both an audible alarm and a counter with the device so that user feedback may be audible as well as numeric indicating correct push-ups accomplished and the number thereof.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims, and by their equivalents.

What is claimed is:

1. A configurable push up kit of parts comprising:
   (a) a sizing unit for measuring a user's lower arm length;
   (b) a plurality of arm length extenders which are selected as a pair based upon said user's lower arm length measurement; and
   (c) a guidebox component further comprising a pair of hollow tubes capable of receiving said selected pair of arm length extenders and thereby positioning one end of each of said arm length extenders at a height representing a preferred lower range of motion point for a push up exercise for said user based upon said user's lower arm length.

2. The configurable push up kit of parts of claim 1 wherein said arm length extender pairs are the same length as one another.

3. The configurable push up kit of parts of claim 1 further comprising an audible alarm which is activated upon the user performing a push up which satisfies a predetermined lower range of motion requirement.

4. The configurable rush up kit of parts of claim 1 further comprising a counter which counts the number of push-ups which are performed and which meet a predetermined lower range of motion requirement.

5. The configurable push-up kit of parts of claim 1 wherein said hollow tubes located on said guidebox are laterally movable so as to permit adjustments for user upper body breadth.

6. The push up device of claim 1 where said user's lower arm length measurement reflects the distance from just below the user's bicep to the middle of the user's palm.

7. The push up device of claim 1 where said plurality of arm length extenders comprise tubes of varying lengths that are selected to address a range of user lower arm length measurements.

8. The push up device of claim 7 wherein said range of user lower arm length measurements accommodated by a single pair of arm length extenders is approximately one inch.

9. The push up device of claim 7 wherein said arm length extender sizes comprise pairs of 9", 10", 11", 12" and 13" arm length extenders.

10. The push up device of claim 1 wherein said arm length extenders and said hollow tubes are formed from PVC tubing.

11. The push up device of claim 4 further comprising an audible alarm which is activated upon the user performing a push up which satisfies a predetermined lower range of motion requirement.

12. A method of providing range of motion feedback to a user performing a push up comprising the steps of:
   (a) measuring a user's lower arm length;
   (b) selecting a pair of arm length extenders from among a plurality of arm length extenders based upon said user's lower arm length measurement; and
   (c) inserting said selected pair of arm length extenders into a pair of hollow tubes located upon a guidebox, said pair of hollow tubes capable of receiving said selected pair of arm length extenders and thereby positioning one end of each of said arm length extenders at a height representing a preferred lower range of motion point for a push up exercise for said user based upon said user's lower arm length.

13. The method of claim 12 further comprising the step of activating an audible alarm upon the user performing a push up which satisfies a predetermined lower range of motion requirement.

14. The method of claim 12 further comprising the step of incrementing a counter which counts the number of push-ups which are performed and which meet a predetermined lower range of motion requirement upon the performance of such a push up which meets said predetermined lower range of motion requirement.

15. The method of claim 14 further comprising the step of activating an audible alarm upon the user performing a push up which satisfies a predetermined lower range of motion requirement.

* * * * *